United States Patent
De Baerdemaeker et al.

(10) Patent No.: US 6,998,559 B2
(45) Date of Patent: Feb. 14, 2006

(54) DETECTION SYSTEM FOR SORTING APPARATUS

(75) Inventors: Josse De Baerdemaeker, Heverlee (BE); Peter Coucke, Heverlee (BE); Leonardus Paulus Crezee, Snelrewaard (NL)

(73) Assignee: FPS Food Processing Systems B.V., (NL)

( * ) Notice: Subject to any disclaimer, the term of this patent is extended or adjusted under 35 U.S.C. 154(b) by 143 days.

(21) Appl. No.: 10/296,641

(22) PCT Filed: May 28, 2001

(86) PCT No.: PCT/NL01/00397

§ 371 (c)(1),
(2), (4) Date: Jun. 3, 2003

(87) PCT Pub. No.: WO01/92873

PCT Pub. Date: Dec. 6, 2001

(65) Prior Publication Data

US 2003/0201209 A1    Oct. 30, 2003

(30) Foreign Application Priority Data

May 29, 2000  (EP) .................................. 00201864

(51) Int. Cl.
*G01N 3/40* (2006.01)

(52) U.S. Cl. ...................... 209/590; 209/599; 209/518; 209/520; 73/12.09; 73/632; 73/818

(58) Field of Classification Search ..................... None

See application file for complete search history.

(56) References Cited

U.S. PATENT DOCUMENTS

| | | | | |
|---|---|---|---|---|
| 2,277,037 A | * | 3/1942 | Clark et al. ................... | 73/596 |
| 3,067,605 A | * | 12/1962 | Bliss ......................... | 73/12.09 |
| 4,466,543 A | * | 8/1984 | Zwahlen et al. ............. | 209/556 |
| 4,625,872 A | * | 12/1986 | DeLacy et al. .............. | 209/557 |
| 4,884,696 A | * | 12/1989 | Peleg .......................... | 209/545 |
| 5,152,401 A | * | 10/1992 | Affeldt et al. .............. | 209/556 |
| 5,315,879 A | * | 5/1994 | Crochon et al. ............. | 73/818 |

(Continued)

FOREIGN PATENT DOCUMENTS

JP         401217255 A  *  8/1989   ................. 209/599

(Continued)

*Primary Examiner*—Donald P. Walsh
*Assistant Examiner*—Jonathan R Miller
(74) *Attorney, Agent, or Firm*—Stites & Harbison PLLC; Marvin Petry

(57) ABSTRACT

The present invention relates to a system for determining characteristics of products of generally unequal size, e.g. apples, which are conveyed on product carriers, such as rollers of a conveying apparatus, and pass the system, the system comprising a detection device, arranged at some distance from the products, having a transmitter section and a receiver section, as well as a signal processing unit for processing signals to and from the system, including the signals of the receiver section for determining the characteristics, the system further comprising: a sensor which, prior to the passage of a product, scans the size of each passing product and produces a corresponding scanning signal, and a displacement device, for positioning, in accordance with each scanning signal, at least the receiver section of the detection device at a well-defined distance during the passage of each product. With such a system, in an advantageous manner, on-line, characteristics such as firmness and sugar content of fruits can be determined. These characteristics can be used real-time as a selection criterion during sorting of large amounts of fruits.

17 Claims, 5 Drawing Sheets

U.S. PATENT DOCUMENTS

Figure 1:
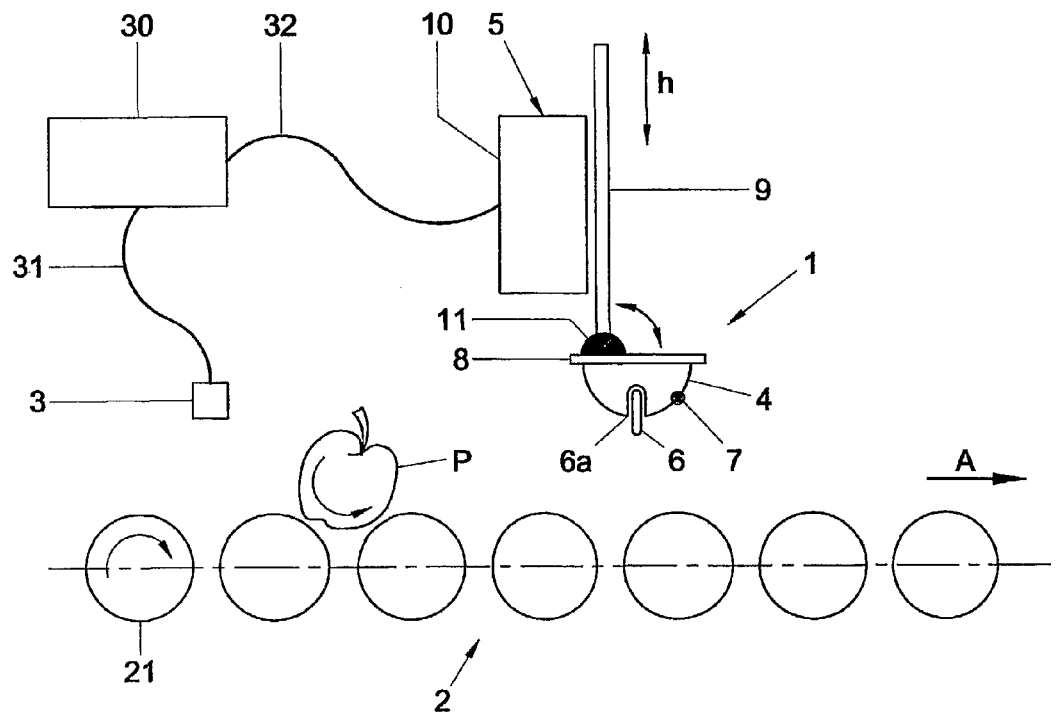

| | | | | |
|---|---|---|---|---|
| 5,691,473 A | * | 11/1997 | Peleg | 73/573 |
| 5,696,325 A | * | 12/1997 | Coucke et al. | 73/595 |
| 5,811,680 A | * | 9/1998 | Galili et al. | 73/579 |
| 5,918,266 A | * | 6/1999 | Robinson | 73/37.5 |
| 6,026,686 A | * | 2/2000 | Hattori et al. | 73/579 |
| 6,276,536 B1 | * | 8/2001 | Terasaki et al. | 209/599 |
| 6,410,872 B1 | * | 6/2002 | Campbell et al. | 209/577 |
| 6,435,002 B1 | * | 8/2002 | Briggs | 73/23.2 |
| 6,722,201 B1 | * | 4/2004 | De Baerdemaeker et al. | 73/627 |

FOREIGN PATENT DOCUMENTS

| | | | | |
|---|---|---|---|---|
| JP | 402310465 A | * | 12/1990 | 73/12.14 |
| JP | 403095455 A | * | 4/1991 | 73/12.12 |

* cited by examiner

DETECTION SYSTEM FOR SORTING APPARATUS

The present invention relates to a system for determining characteristics of products which are conveyed on a conveying apparatus and pass the system.

More particularly, the invention relates to a system for determining characteristics of products of generally unequal size, e.g. apples, which are conveyed on product carriers, such as rollers of a conveying apparatus, and pass the system, the system comprising a conveying apparatus for continuously conveying product carriers, a detection device, arranged at some distance from the products, with a transmitter section and a receiver section, as well as a signal processing unit for processing signals to and from the system, including the signals of the receiver section for determining the characteristics.

Such systems are generally known in the art of selecting and sorting products, such as fruit, vegetables, and eggs. WO98/52037, for instance, discloses a device with a transmitter and receiver, in particular for tapping fruit and then recording the tap signal, which device comes down under spring action from one product onto the next product passing under it, this device rolling over such a product as it passes. During this rolling movement, tapping and recording take place.

Such a device has the disadvantage that, in particular in making a transition from the clearly smaller to the considerably larger products and following same, a relatively great difference in height is to be bridged. The consequent coming down onto a next product from some height may cause damage, certainly in the case of delicate products, such as, for instance, pears. Moreover, the operation of this device will be substantially limited to a vertical plane.

To remedy the drawbacks mentioned, the system according to the invention is characterized in that the system further comprises:

a sensor arranged for, prior to the passage of a product, scannings the size of each passing product and producing a corresponding scanning signal, and a displacement device, arranged for positioning, in accordance with each scanning signal, at least the receiver section of the detection device at a well-defined distance during the passage of each product.

In an advantageous manner, measurements are thus obtained which are comparable for the successive products. Moreover, damage to products which are being conveyed with the conveying apparatus, such as, for instance, a conveying apparatus with rollers or diabolos mounted on shafts which are advanced by endless chains, can be prevented.

In a particular embodiment of the present invention, the transmitter section comprises a tapping device and the receiver section comprises a microphone, which are both accommodated in the same housing.

According to a further embodiment, the tapping device comprises a tapping rod which is movable in a guide tube, the tapping device being energized such that during the passage of the product the tapping rod is moved to the product and, after tapping the product, is retracted.

In another exemplary embodiment, the present invention is characterized in that the receiver section comprises a microphone accommodated in a housing, and that the transmitter section, being spring-mounted with a clamping device between the product carriers and moving along with the conveying apparatus, comprises a tapping rod which, when passing the receiver section, is brought out of its equilibrium position, taps the product and moves back.

To be seen as a great advantage of this alternative exemplary embodiment is the flexibility in positioning the receiver, so that in this way, for different types of fruits, such as, for instance, apples, pears, kiwis, and melons, an optimum measuring signal can be obtained.

It should be noted that JP 03 039649 discloses a device for measuring the internal quality of fruits by tapping on the fruit and by detecting an oscillating wave of vegetable or fruit with a sensor. The known device analyses the waveform and compares the waveform with standard values to decide the grade of the fruit or vegetable. The shock or tapping means 4 and the sensor means 32 are positioned relative to the fruit or vegetable based on a measurement of the size of the fruit which measurement is performed before the measurement of the internal quality. As is clear from FIGS. 1, 8 and 10 of the Japanese publication, the shock means 4 and at least one of the sensor parts 32 extend in the transport path of the fruit when the measurement takes place in a measurement position. Consequently, it is necessary that the shock means 4 and the said sensor part 32 extending in the transport path of the fruit are removed from this path by lifting the sensor parts 32 and the shock means 4 with the lifting piston 331 when a next fruit or vegetable has to be positioned in the measurement position. In view of the fact that the sensor part 32 extending in the transport path is in contact with the fruit or vegetable when the measurement takes place, it is inevitable that the fruit or vegetable is stationary when the measurement of the internal quality is performed. After said quality measurement, the sensor parts 32 and the shock means 4 are lifted again and the next fruit is positioned in the measurement position. There is no disclosure in this document for a continuously moving conveyor on which the measurement of the internal quality is performed.

Further, the system according to the invention is characterized in that the direction of movement of the tapping rod is vertical.

This embodiment makes it possible to accurately tailor the movement of the tapping rod to its weight, and hence to control the impact on the fruit.

Figure 2:
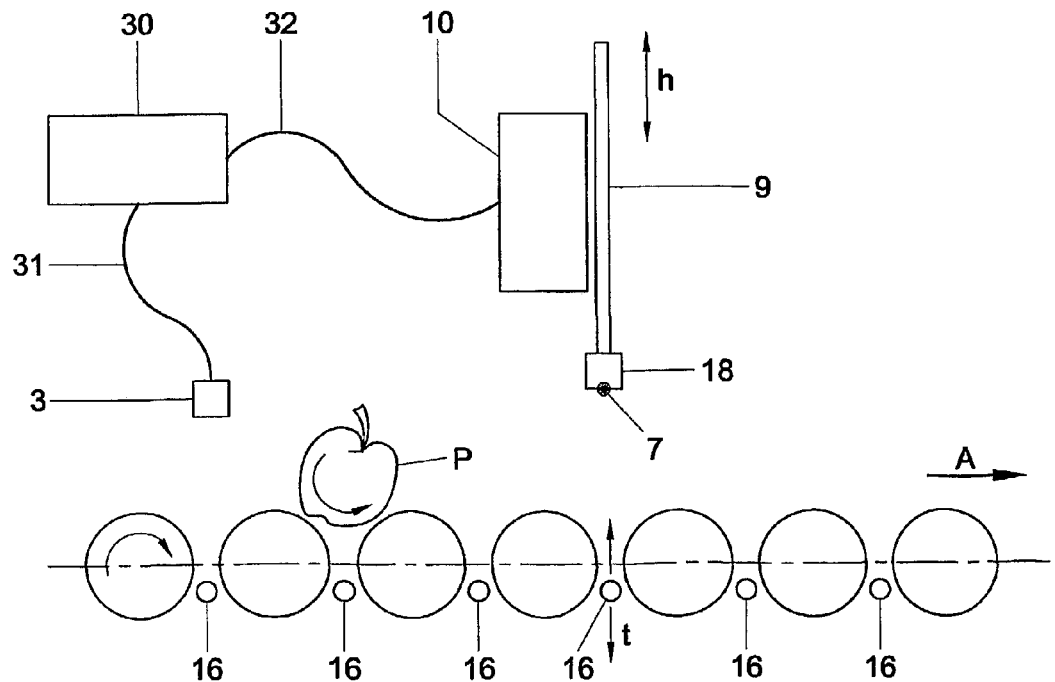
Figure 3:
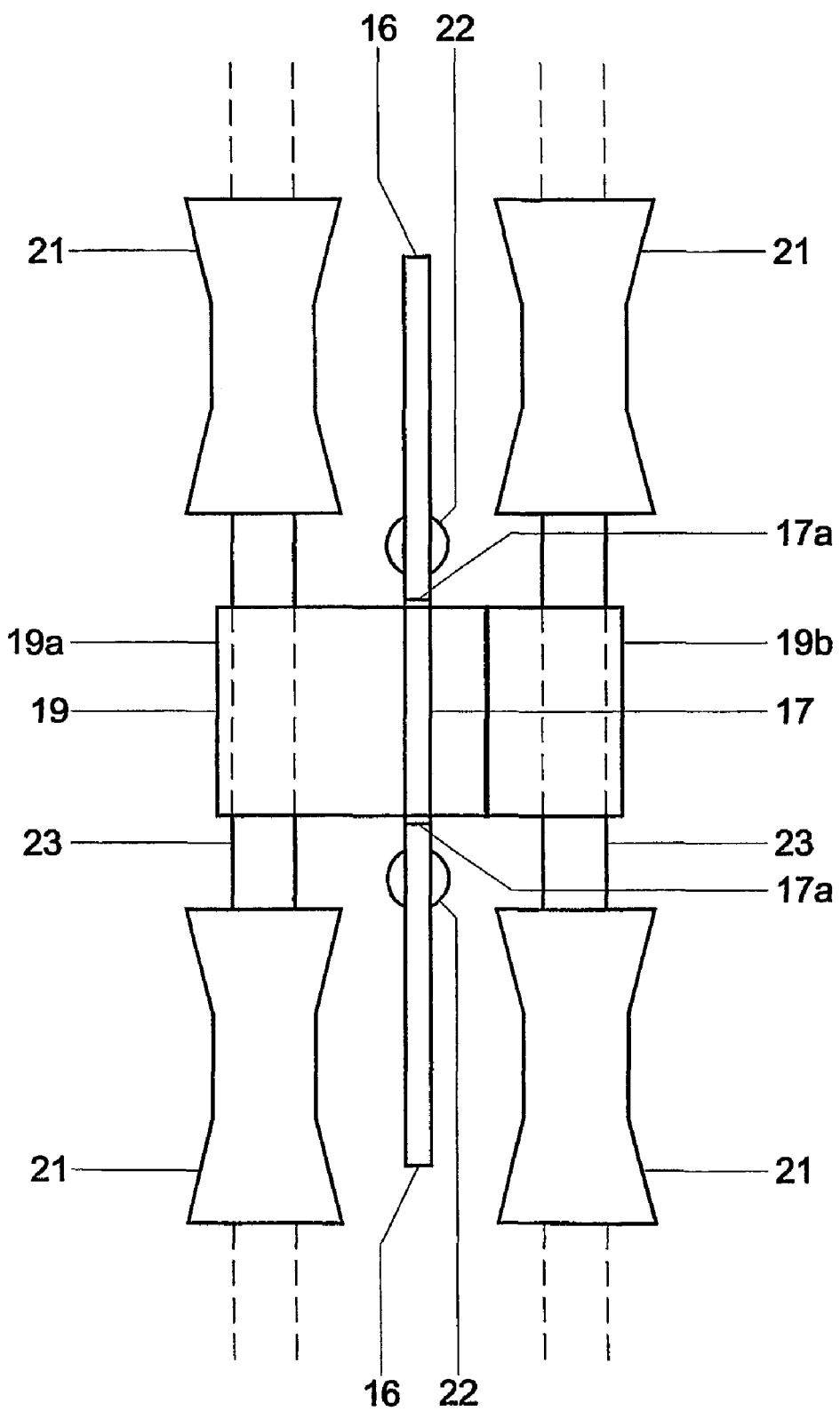
Figure 4:
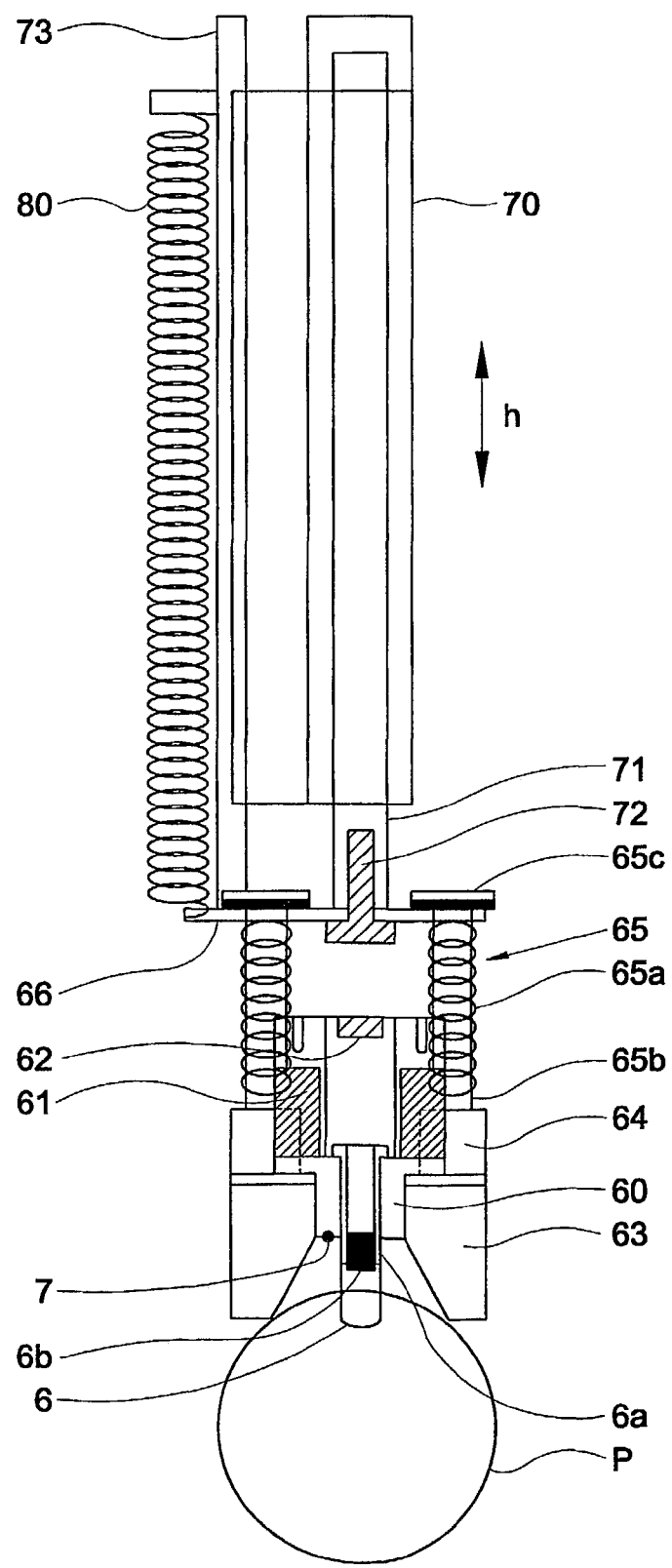

The present invention will be further elucidated hereinafter with reference to the accompanying drawings, in which:

FIG. 1 schematically shows an elevation of a first embodiment of the present invention;

FIG. 2 schematically shows an elevation of a second embodiment of the present invention;

FIG. 3 schematically shows a further detail of the second embodiment in top plan view;

FIG. 4 schematically shows a third exemplary embodiment of the invention; and

Figure 5:
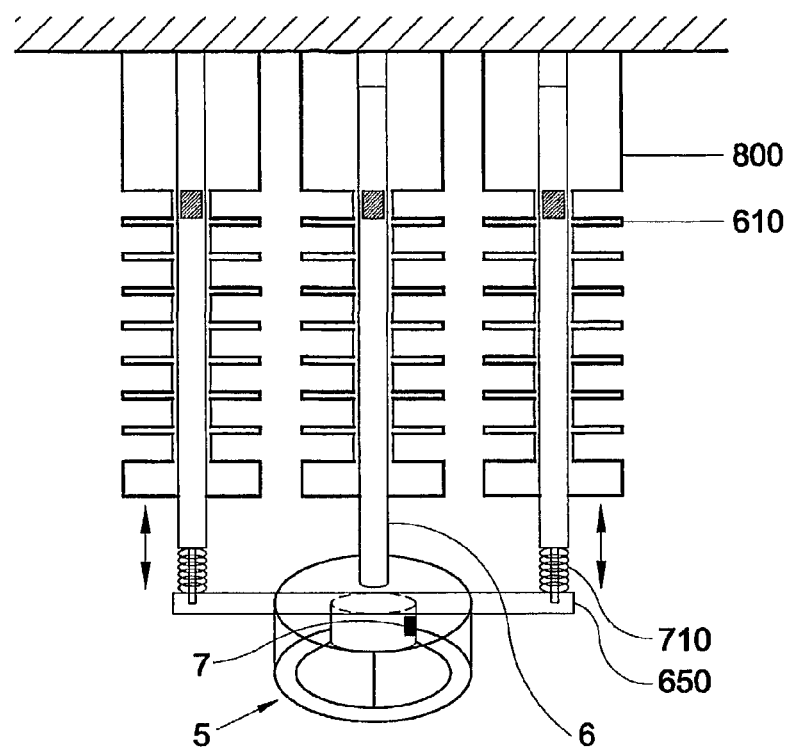
Figure 6:
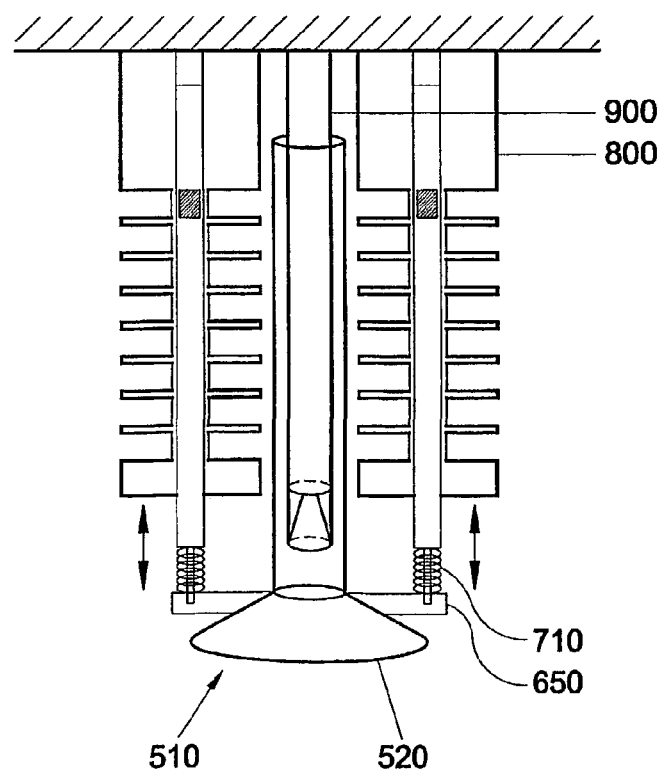
Figure 7:
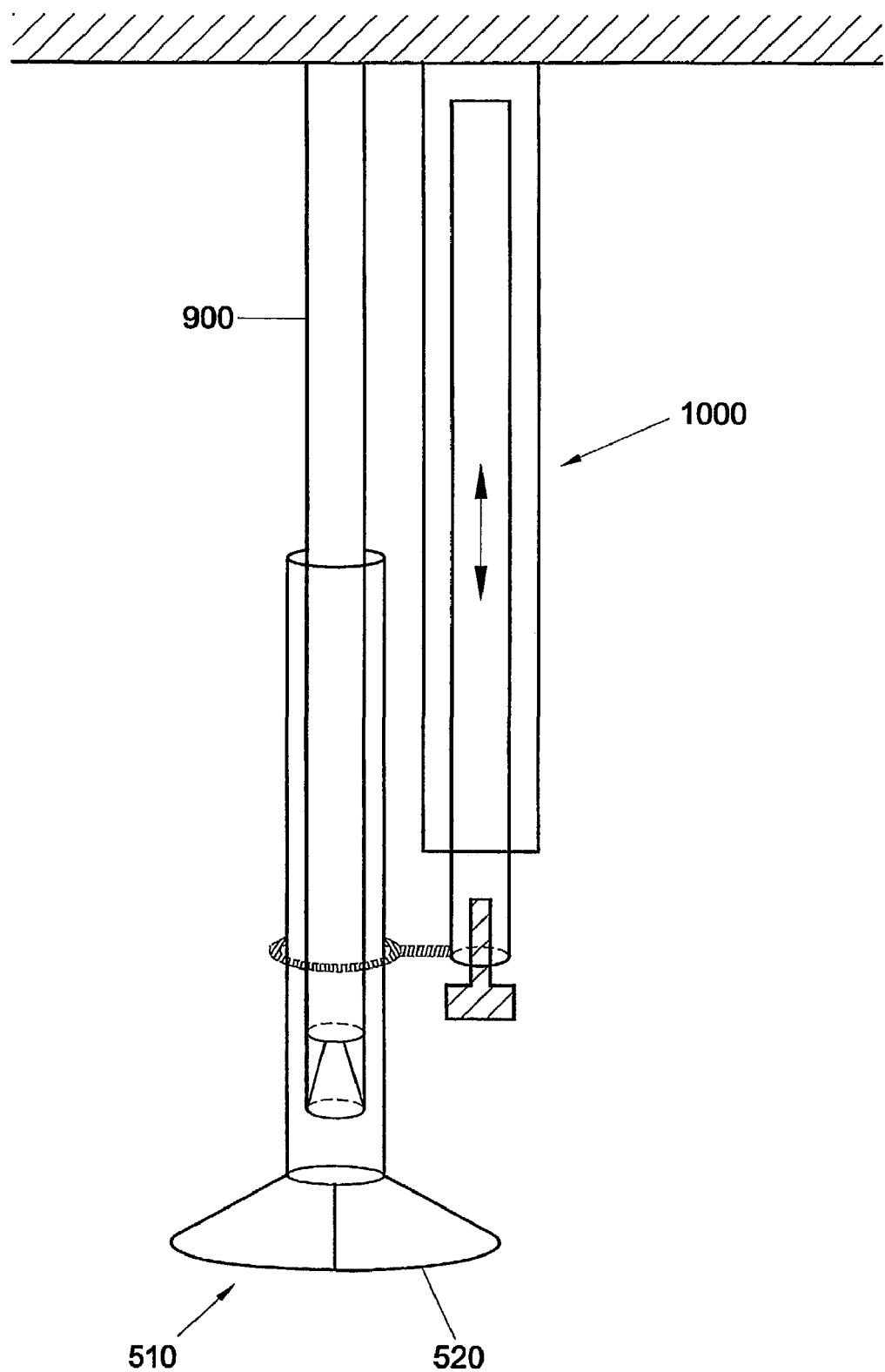

FIGS. 5, 6 and 7 show slightly modified exemplary embodiments.

FIG. 1 shows a detection system 1 above a roller conveyor 2, with products P disposed on rollers 21, usually hourglass-shaped. These rollers 21 are customarily mounted on shafts arranged between, for instance, two endless chains and advanced in the direction of arrow A by means of a gear driven by a motor (not shown in the drawing for clarity). If necessary, the rollers 21 themselves may be rotated, for instance as indicated by the arrow, so that, as a result, the products will rotate as well. This may be necessary, for instance, when several points on the product are to be probed, for instance by tapping or also for obtaining optical data.

With a distance sensor 3, for instance a photoelectric cell or camera, the size, or also the height, of the product P is determined, and the associated scanning signal is transmitted along signal path 31, for instance a cord or optical fiber, to a signal processing device 30, for instance a computer. Thereafter, in accordance with this scanning signal, a control signal is supplied via signal path 32 to a detection device 5, for it to be positioned at the proper height when the product P passes. This detection device comprises a transmitter section and a receiver section, which will be described hereinafter in more detail.

FIG. 1 schematically shows an exemplary embodiment of a detection device 5, with transmitter and receiver accommodated as a single unit 4 in a housing or holder 8. The transmitter is formed by a tapping device, in particular a tapping rod 6, which, as indicated, is vertically movable in a guide tube 6a. The drive can be effected in a variety of ways, such as, for instance, electromagnetically or magnetically, or through a combination thereof, or also with a mechanical spring system. The receiver comprises a microphone 7 which, after the product has been tapped, records the sound produced. Signals for driving the transmitter and for processing the signals of the receiver are processed in a conventional manner in computer 30, for which purpose the signals are guided again along the same, or a similar, signal path 32. With such a tapping device, the hardness, also called firmness, of a product, such as an apple, tomato, or kiwi, can be determined on-line during sorting on a sorting machine, and in this manner, often real-time, serve also as a selection criterion.

The vertical displacement in the direction h indicated is provided by bar 9 which is connected with the housing 8 through a connecting element 11. This connecting element 11 can be, for instance, a spring-biased pivot. With driving unit 10, for instance a stepping motor, in particular a linear stepping motor, for instance with servo control, the bar 9 can, in accordance with the scanning signal of sensor 3, be steered in the right direction and to the correct height. The detection device can moreover be so designed that a part of housing 8 is formed from resilient material, so that during tapping the housing is pressed slightly onto and against the product. It will be clear to anyone skilled in the art that other types of transmitters and receivers, such as laser means or piezo elements, can be used.

FIGS. 2 and 3 show a second exemplary embodiment according to the invention, in which the transmitter and receiver are not accommodated in the same housing. The transmitter, represented in more detail in FIG. 3, is an array of tapping rods 16, vertically displaceable between the rollers in a plane parallel to the roller shafts 23, being connected through a generally resilient bending portion 17a with a central holding element 17, this holding element in turn being mounted with two clamping halves 19a and 19b of clamp 19, which is clamped between the shafts 23 of the roller conveyor 2. These clamping halves can, for instance through a sliding connection, move relative to each other, to thereby take up the increase in distance between the shafts upon a change in the direction of movement when the endless conveyor passes through a bend. Activation of the transmitter takes place by leading the cam blocks 22 mounted on the rods 16, prior to tapping, over a cog (not shown) positioned under the rollers, and subsequently allowing them to spring back, the deflection being such that the product will be tapped from below. The receiver, a microphone 7, in this embodiment is accommodated in a housing 18, which in turn is mounted on a bar 9, which in turn is driven by a drive 10. It will be clear to anyone skilled in the art that the tapping movement of these rods 16 can also be effected in a different manner, for instance electromagnetically. In this exemplary embodiment, it is also possible to use the above-mentioned receivers, viz. laser means or piezo elements.

The above embodiments show that with small modifications, measurements can also be performed in other planes than the above-mentioned vertical plane. This can be of great advantage both in tapping measurements aimed at receiving resonance signals, and in optical measurements to determine absorption and/or reflection coefficients, both often direction-dependent. Moreover, a further modification will enable a rotation of the detection device in the vertical plane, yielding a positioning not only in terms of distance but also at an angle.

In particular for the above-mentioned optical measurements, the rotation referred to could be of importance. When with the detection device absorption and/or reflection of well-defined wavelengths of light irradiated onto fruits is/are to be determined, for instance to determine sugar content, moisture content, water concentration, or acidity, a combination of measurements in several directions may be required.

In view of the above, it will be clear to anyone skilled in the art that placing several detection systems along a sorting line can be of great advantage. In this way, sets of measurements for the same fruit can be obtained. Thus, repeat measurements can be performed and selection criteria can be defined more closely, whilst data processing can be carried out automatically in a conventional manner.

In a further embodiment, the embodiments according to FIG. 1 or 2 can be modified such that, instead of the housings 8 and 18, a small wheel, itself mounted, for instance, on the end of an arm which functions as lever, with transmitter and receiver, or receiver alone, mounted on the shaft, is rolled over the products and, as taught by the present invention, when rolling over the products is, in a controlled manner, timely moved with the arm to a next product and from a previous product to prevent undesired impacts.

FIG. 4 shows a third exemplary embodiment according to the invention. The tapping rod 6 having therein a magnet 6b of corresponding, often small, dimensions, is operatively driven downwards and retracted again with an electromagnet. This electromagnet consists of a coil housing 60 and a coil 61. Again, the tapping rod 6 is movable in a guide tube 6a, which is formed in the coil housing 60. Also accommodated in the coil housing is the microphone 7. After performing the tapping movement, the tapping rod is retracted and then butts at the end of the guide tube against a buffer block 62.

The positioning of this detection system at the proper height above a product P is done with a linear motor 70, having therein a movement shaft 71 which is mounted with a mounting screw 72 on a mounting plate 66 connected with the coil housing 60.

To place the unit with tapping rod on a product P in proper contact, a bush 63 is provided. This bush can be substantially circular-symmetrical, but may also consist of two elongate, mutually symmetrical halves. Furthermore, a spring coupling with the coil housing has been obtained by means of buffer rubbers 64 and spring elements 65, of great advantage both in the proper positioning of the detection device and in taking up unexpected and large shocks. In particular, these spring elements consist of a stem 65b, resiliently connected with a buffer rubber 64 and attached at its upper end, through a hole in the mounting plate 66, to a cover plate 65c. A compression spring 65a around the stem 65b presses the cover plate 65c against the plate 66. It will be clear to anyone skilled in the art that the hole-stem connection allows a flexible positioning of the detection device in a highly suitable manner. Conventionally, there are provided four spring elements 65, viz. one at each corner, but other geometries can be used as well.

In order to prevent undesired rotation between the mounting plate and the upper end of the linear motor, there extends along the motor a guide tube or bar 73, along which the motor can move in the intended direction.

Also extending in the direction of displacement of the motor, a draw spring 80 is tensioned, to pull the motor from the product immediately in the event of an energization drop-out, to thereby prevent damage to any further passing products. It will be clear to anyone skilled in the art that the strength of this spring is chosen such that in normal use the motor will not in any way be hindered by it.

In an embodiment not shown, as a connecting element, a curve with follower can be arranged, so as to have the detection device follow a well-defined curve during measurement.

In FIGS. 5, 6 and 7, slightly modified exemplary embodiments are shown.

FIG. 5 schematically represents three coil units mounted side by side on the sorting machine. Coils 610 of linear motors with cores 710 are attached to the sorting machine with mounting blocks 800. The two outermost motors are connected with the detection device 5 which can be placed on a passing product. Damping elements 650 provide for a suitable placement on the product. Likewise with a linear motor, the central core with tapper can be driven.

FIGS. 6 and 7 concern a detection device 510 for light, having in particular a light receiving device 900, for instance a fiber. A screening cap portion 520 of this detection device can be placed on a passing product with two units with mounting blocks 800, coils 610, and cores of a linear motor, or with a linear motor 1000, both mounted on the sorting machine again. In this way, the collection or reception of both incident scattered light and reflective incident light can be effectively avoided.

An advantage of the use of linear motors is the possibility of suitably choosing parameters such as speed and mass. These embodiments have been found to allow sorting at passing speeds of up to 10 to 20 products per second.

It will be clear to anyone skilled in the art that small modifications can be made in the exemplary embodiments herein, which are understood to fall within the scope of the appended claims.

What is claimed is:

1. A system for determining characteristics of products of generally unequal size, which are conveyed on product carriers, and pass the system, the system comprising:
   a conveying apparatus for continuously conveying product carriers,
   a detection device, arranged at some distance from the products, having a transmitter section and a receiver section,
   a signal processing unit for processing signals to and from the system, including the signals of the receiver section for determining the characteristics,
   a sensor arranged for, prior to the passage of a product, scanning the size of each passing product and producing a corresponding scanning signal, and
   a displacement device, for positioning, in accordance with each scanning signal, at least the receiver section of the detection device at a well-defined distance during the passage of each product.

2. A system according to claim 1, characterized in that the transmitter section comprises a tapping device and the receiver section comprises a microphone which are both accommodated in the same housing.

3. A system according to claim 2, characterized in that the tapping device comprises a tapping rod which is movable in a guide tube, the tapping device being energized such that during the passage of the product the tapping rod is moved to the product and after tapping the product is retracted.

4. A system according to claim 3, characterized in that the direction of movement of the tapping rod is vertical.

5. A system according to claim 3, characterized in that the guide tube is a part of an electromagnet with coil housing and coil, the coil housing being connected with the displacement device through spring elements.

6. A system according to claim 5, characterized in that the coil housing is connected with the displacement device through four spring elements.

7. A system according to claim 1, characterized in that the receiver section comprises a microphone accommodated in a housing, and that the transmitter section, spring-mounted between the product carriers with a clamping device and moving along with the conveying apparatus, comprises a tapping rod which, when passing the receiver section, is brought out of an equilibrium position, taps the product and moves back.

8. A system according to claim 7, characterized in that the direction of movement of the tapping rod is vertical.

9. A system according to claim 7, characterized in that the products of generally unequal size are apples.

10. A system according to claim 7, characterized in that the product carriers are rollers of a conveying apparatus.

11. A system according to claim 1, characterized in that both the receiver section and the transmitter section are positioned at a well-defined distance.

12. A system according to claim 11, characterized in that each section is positioned with a linear motor.

13. A system according to claim 1, characterized in that the detection device comprises a light receiving device.

14. A system according to claim 13, characterized in that, on the light receiving device, a screening cap portion is positioned.

15. A system according to claim 14, characterized in that the screening cap portion is positioned with at least one linear motor.

16. A device according to claim 1, characterized in that in the displacement device a connecting element is accommodated, allowing well-defined angles in a substantially vertical plane to be assumed.

17. A device according to claim 16, characterized in that said connecting element comprises a curve with follower.

* * * * *